United States Patent
Erickson et al.

(10) Patent No.: US 9,566,128 B2
(45) Date of Patent: Feb. 14, 2017

(54) SHIPPING AND AGGREGATION SYSTEM FOR MEDICAL SHARPS

(75) Inventors: Thomas E. Erickson, Crosslake, MN (US); James J. Erickson, Mound, MN (US); Thomas Sauro, Rosemount, MN (US)

(73) Assignee: ULTIMED INC., Excelsior, MN (US)

( * ) Notice: Subject to any disclaimer, the term of this patent is extended or adjusted under 35 U.S.C. 154(b) by 2181 days.

(21) Appl. No.: 12/570,730

(22) Filed: Sep. 30, 2009

(65) Prior Publication Data

US 2011/0073508 A1 Mar. 31, 2011

(51) Int. Cl.
*A61B 50/30* (2016.01)
*A61B 17/00* (2006.01)
*A61M 5/00* (2006.01)
*A61M 5/32* (2006.01)

(52) U.S. Cl.
CPC .......... *A61B 50/362* (2016.02); *A61B 50/3001* (2016.02); *A61B 2017/00398* (2013.01); *A61B 2050/006* (2016.02); *A61B 2050/009* (2016.02); *A61B 2050/0057* (2016.02); *A61B 2050/0066* (2016.02); *A61B 2050/0074* (2016.02); *A61B 2050/3008* (2016.02); *A61B 2090/0807* (2016.02); *A61M 5/002* (2013.01); *A61M 5/3205* (2013.01)

(58) Field of Classification Search
CPC ........................... A61B 50/362; A61B 50/3001
USPC .................................. 206/366, 205; 220/507
See application file for complete search history.

(56) References Cited

U.S. PATENT DOCUMENTS

| | | | |
|---|---|---|---|
| 3,348,894 A | 10/1967 | De Berry | |
| 4,886,164 A | 12/1989 | Stein et al. | |
| 4,919,264 A * | 4/1990 | Shinall | 206/210 |
| 4,964,509 A | 10/1990 | Insley et al. | |
| 5,062,527 A | 11/1991 | Westerman | |
| 5,230,426 A * | 7/1993 | Keefe et al. | 206/205 |
| 5,236,088 A | 8/1993 | Dhority et al. | |
| 5,236,099 A | 8/1993 | Fties et al. | |
| 5,427,238 A | 6/1995 | Weiss | |
| 5,465,841 A | 11/1995 | Wilson et al. | |
| 5,469,691 A | 11/1995 | Grey et al. | |
| 5,474,180 A | 12/1995 | Robinson et al. | |
| 5,511,657 A | 4/1996 | Gnau, III et al. | |
| 5,570,783 A | 11/1996 | Thorne et al. | |
| 5,630,506 A | 5/1997 | Thorne et al. | |
| 5,873,462 A * | 2/1999 | Nguyen et al. | 206/366 |
| 5,996,799 A | 12/1999 | Garreth et al. | |
| 6,116,461 A * | 9/2000 | Broadfield et al. | 221/98 |
| 7,159,714 B2 | 1/2007 | Wilkinson et al. | |
| 7,428,807 B2 | 9/2008 | Vander Bush et al. | |

(Continued)

FOREIGN PATENT DOCUMENTS

EP 1669097 A2 6/2006

*Primary Examiner* — Anthony Stashick
*Assistant Examiner* — Raven Collins
(74) *Attorney, Agent, or Firm* — Seager, Tufte & Wickhem LLP (57) ABSTRACT

The disclosure relates to a container for shipping, storing, dispensing, and receiving units for storing, dispensing, and receiving medical sharps, wherein the container includes a plurality of compartments, said compartments each being capable of containing one unit for storing, dispensing, and receiving medical sharps and to a method of using said container to store, dispense, receive, and ship said units.

30 Claims, 7 Drawing Sheets

(56) References Cited

U.S. PATENT DOCUMENTS

2004/0040873 A1 3/2004 Koseki
2005/0072124 A1 4/2005 Jaycox
2006/0253297 A1 11/2006 Mallett et al.
2007/0001839 A1 1/2007 Cambre et al.

* cited by examiner

SHIPPING AND AGGREGATION SYSTEM FOR MEDICAL SHARPS

TECHNICAL FIELD

This disclosure relates generally to the distribution of unused medical sharps and the consolidation and return of used medical sharps.

BACKGROUND

Because of well known health issues, the safe disposal of syringes and other "sharps" has long been a high priority for medical related professional facilities and industries. An increasing number of individuals are using medical sharps in private and public settings which use potentially creates a source of used and contaminated sharps outside of a relatively well controlled environment with established disposal protocols and collection points.

Medical delivery pens (hereinafter sometimes "MDPs") have, more recently, become widely used instead of or in addition to syringes, e.g., by diabetics, who frequently inject themselves several times a day with accurately measured, adjustable, pre-selected amounts of insulin or other medication. Medical delivery pens include a reservoir of medication and a distal end adapted to be attached (usually by thread means) to a pen needle assembly (PNA). The pen needle assemblies typically include a removable thin sterile seal covering the proximal (large diameter) end of the said outer shield and a removable tube-like shield covering the distal portion of the hollow needle. The assembled pen needle assembly is then factory sterilized. The user of a pen needle assembly removes the seal from the outer shield, screws the pen into the proximal end of the pen needle housing, removes the outer and tube-like shields, sets the medical delivery pen for the desired dose of medication, and then inserts the distal end of the pen needle into the target tissue following which the medical delivery pen is actuated to deliver the desired dose of medication through the hollow needle into said tissue.

Many diabetics routinely administer medication to themselves several times a day by injection of a pre-selected quantity of insulin (or substitute medication) in liquid form; the correct amount of medication can be determined from prior professional medical instruction or by use of convenient portable blood analysis kits which are small, compact and provide rapid indicators of the user's blood sugar level. The several daily injections are often done away from the diabetic's home or residence which has made the use of the portable, convenient medical delivery pens widespread. The aforesaid testing kits and the medical delivery pens are relatively small in size and can easily fit within a woman's purse or equivalent. A typical scenario for a diabetic at a restaurant for a meal is to first use the blood sugar testing kit to obtain an indicator of his or her blood sugar level. This information then facilitates programming or adjusting the medical delivery pen to deliver the desired quantity of medication. Then the pen with an attached PN (a PNA sans the outer protective shield) is used to inject the medication. These steps require a relatively short length of time and can be done with minimum loss of privacy.

MDPs are also widely used by doctors, nurses and other professionals in their duties. Many individuals will request (sometimes insist) that an injection be done with a pen needle rather than a syringe.

Devices which dispense unused pen needle assemblies and subsequently receive and store used pen needle assemblies are now available and are well accepted for convenience and safety in minimizing user contact with used medical sharps; however the used sharps must still be treated with caution until they are returned to an appropriate medical waste facility. Larger facilities such as hospitals and clinics typically have regularly scheduled services which collect containers of medical waste and used medical sharps. In areas where such routine collection of medical waste is not readily available, it would be desirable to provide a system and method of consolidating medical sharps containers and packaging the consolidated material for return to an appropriate medical waste treatment facility. Often this may be conveniently accomplished at a facility such as a pharmacy which originally dispensed the medical sharps.

SUMMARY

This disclosure pertains to a container for distributing, storing, dispensing, and receiving for units for storing, dispensing, and receiving medical sharps comprising an outer container including plurality of inner compartments, said compartments each being capable of containing one unit for storing, dispensing, and receiving medical sharps. The container is adapted to store and dispense units containing unused sharps and to receive and store units containing used medical sharps. In addition, the outer container is adapted to differentiate units containing unused sharps from units containing used sharps.

In another embodiment, the disclosure pertains to system for distributing and dispensing unused sharps and returning used sharps comprising a plurality of units for storing, dispensing, and receiving medical sharps; a container for the plurality of units for storing, dispensing, and receiving medical sharps, wherein the container includes a plurality of compartments, each compartment being capable of containing one unit for storing, dispensing, and receiving medical sharps; and wherein the container is adapted to differentiate units containing unused sharps from units containing used sharps. The system also includes a primary container capable of receiving and sealably containing the plurality of units and a secondary container capable of receiving and sealably containing the primary container such that the sealed containers may be shipped by a common carrier such as the United States Postal Service.

The disclosure also encompasses a method of distributing unused medical sharps and collecting used medical sharps comprising providing a plurality of units for storing, dispensing, and receiving medical sharps; providing a container for the plurality of units for storing, dispensing, and receiving medical sharps, said container including a plurality of compartments, each compartment being capable of containing one unit for storing, dispensing, and receiving medical sharps; inserting a unit for storing, dispensing and receiving medical sharps into at least one compartment of the container; and distributing the container containing a plurality of units. The method further comprising dispensing a unit containing unused medical sharps from the container; receiving a unit containing used medical sharps; inserting a unit containing used medical sharps into the container; sealing the container; sealing the container within a secondary container; and shipping the sealed container and secondary container containing a plurality of units containing used medical sharps to a facility for destruction of the used medical sharps.

Although the following description will focus on a container for units containing pen needles and pen needle assemblies for clarity, it will be appreciated that the inventive concept also may be applied to other medical sharps such as hypodermic needles (with or without attached syringe bodies), lancets, and the like.

BRIEF DESCRIPTION OF DRAWINGS

FIGS. 5A-C are details of flange and latching covers useful in various containers of the invention.

FIGS. 6A-B are details of flange and latching covers useful in various containers of the invention.

FIGS. 7A-B are details of flange and latching covers useful in various containers of the invention.

DETAILED DESCRIPTION

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

A variety of units for dispensing unused medical sharps such as pen needles and/or pen needle assemblies, hypodermic needles, and the like as well as receiving and storing those medical sharps following use have been described in the art. These devices are distinguished in that they are capable of storing a quantity of medical sharps before and after use; dispensing unused sharps singly or in small quantities; and receiving as well as storing used sharps following use. Generally these dual purpose units are portable so that a medical sharp may be available for use where and when needed and to limit the time that a used medical sharp is possibly exposed before being returned to protective storage. See U.S. Pat. Nos. 6,685,017; 6,923,318; 6,923,319; and U.S. Published Patent Application 2005/0269227 for nonlimiting examples of such devices.

These units are often distributed through retail channels which sell individual devices loaded with a plurality of medical sharps, pen needle assemblies in the illustrative example to be discussed in greater detail below, to an individual user. It is, however, less common to provide a similarly convenient method to return the used sharps to a medical waste disposal facility and unfortunately a number of such units may find their way into municipal waste streams. While the units do provide protection against accidental sticks and/or contact with any associated bodily fluids, it would be desirable to provide a system which creates a larger number of convenient waste collection points for the safe disposal of units containing used sharps.

This disclosure provides a container which is suited to contain a plurality of units for storing, dispensing, and receiving medical sharps which each have been preloaded with a plurality of unused medical sharps such as pen needle assemblies for distribution through normal retail outlet channels such as pharmacies. Once received, the container may be opened and used to dispense individual units to customers as desired. Used units containing used pen needle assemblies may be returned to the point of sale by a customer and inserted into an unoccupied compartment within the container, often at the same time that a new unit is purchased thereby providing a convenient distribution and disposal loop. When the container is filled with units containing used pen needle assemblies, it may be sealed and packaged appropriately for shipping to a medical waste disposal facility.

Figure 1:
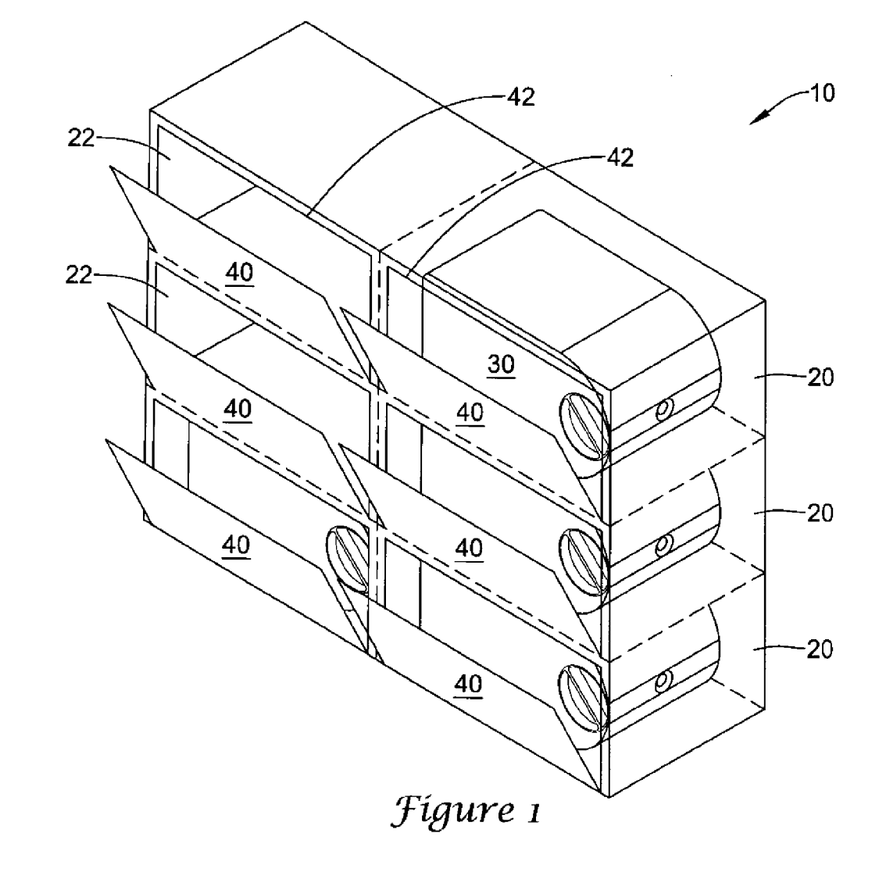
FIG. 1 is a somewhat schematic view of one embodiment of a container for storing, dispensing, and receiving units for storing, dispensing, and receiving medical sharps.

In the embodiment of FIG. 1, container 10 includes a plurality of compartments 20 and/or 22 at least some of which initially contain units 30 for storing, dispensing, and receiving medical sharps. Generally, all compartments 20 will be filled initially with unused units 30, said units containing only unused pen needle assemblies. As illustrated, each compartment 20 is individually accessible through a door 40 and a port 42. During use, one or more of the occupied compartments 20 may become an empty compartment 22 as a unit 30 is removed through port 42 and door 40 and sold or otherwise distributed to the end user of the pen needle assemblies contained within the unit. When a unit (not shown) containing used pen needle assemblies is returned, it is inserted into an empty compartment 22 thereby accumulating and storing units containing used pen needle assemblies. When a sufficient number of units have been returned to the container 10, it may be sealed, packaged and shipped to an appropriate medical waste disposal facility.

Figure 2A:
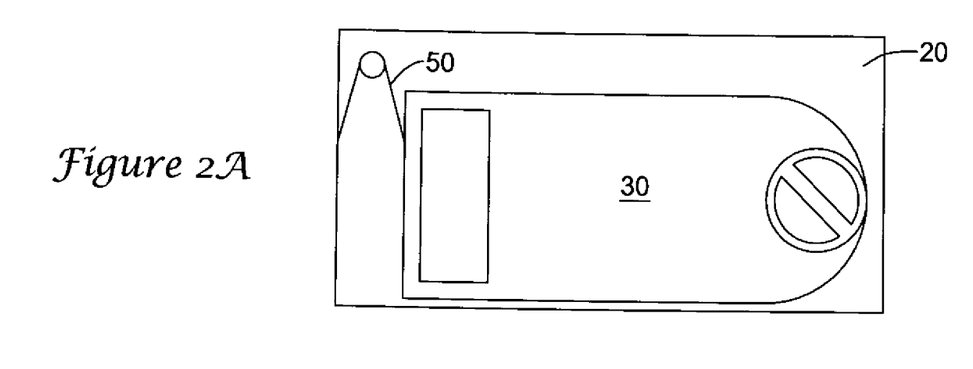
FIGS. 2A and 2B are details of a compartment usable within the embodiment of FIG. 1.
Figure 2B:
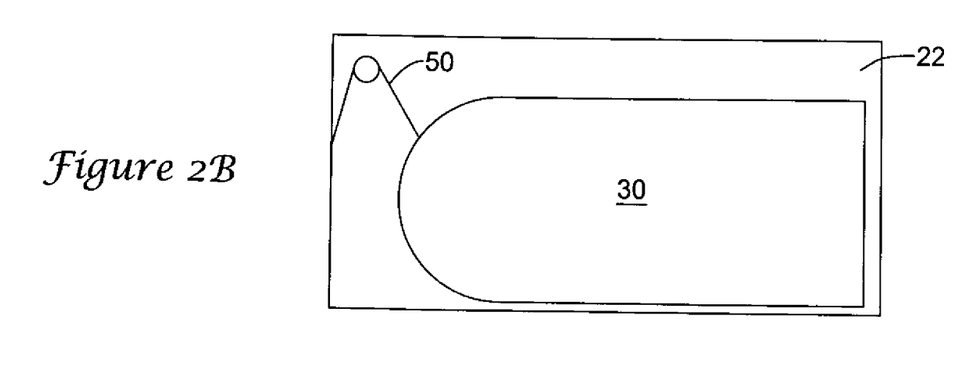

It may be desirable to differentiate units within the container on the basis of whether they contain unused or used pen needle assemblies. This differentiation may be achieved in a number of ways. In some embodiments, the used and unused units may be differentiated by the orientation of the respective units within the container. In FIG. 2A, a compartment 20 contains a unit 30 containing unused pen needle assemblies. As supplied, the unit 30 within the compartment 20 is oriented in a first position which indicates its status as "unused". In this illustrative example the "unused" orientation places a rounded portion of the unit adjacent to the right wall of the compartment 20 and also compresses element 50 causing it to lie generally parallel to the left wall of the compartment 20. Upon removal of the "unused" unit from the compartment, element 50 is released from its compressed state and assumes a second position which changes the effective shape of the compartment and prevents reinsertion of a "used" unit 30 in the "unused" orientation. When the unit 30 is returned to the compartment, it will only fit within the compartment with the rounded portion adjacent to the left wall of the compartment thereby visually indicating its status is "used" as shown in FIG. 2B. In other embodiments, a released element may change the shape of the port 42 through which a "used" unit may be inserted and so may also provide a visual indication of the "unused" or "used" status of a unit within the compartment. Visual indications may be augmented by markings within the compartment which alter their visibility depending upon whether the compartment is occupied by an "unused" or a "used" unit.

It will be appreciated that such visual augmentation may be used whenever the "unused" and "used" unit orientations within a compartment are different or when elements associated with the compartment move in response to the removal or insertion of a unit.

Numerous other means of indicating the status of a unit may be employed. For example, the compartment may include an engaging member which locks to a mating member on the unit such that a "used" unit is prevented from being removed from the compartment, while an "unused" unit is initially positioned such that the engaging member and the mating member do not come in contact. Alternatively, each compartment door 40 may be provided with a latch which allows a unit to be removed, but which locks the compartment when a unit characterized as containing used pen needles has been inserted. Compartment doors 40 may also be provided with seals (not shown) which would provide additional containment for any bodily fluids associated with the used pen needle assemblies. In yet other embodiments, each compartment may be provided with a latching cover which may not be removed once positioned and engaged following insertion of a "used" unit. Such covers may be stored separately and applied as needed or they may be associated with the container by hinges or tethers. In embodiments to be described later, "unused" units may be differentiated from "used" units by their respective positions within the container. For example, "unused" units may be stored near the bottom of the container and "used" units may be stored near the top of the container. Units may be moved within the container manually or may be moved automatically by the operation of the container and the dispensing operation. Removal of an "unused" unit from the bottom of a stack would allow the remaining "unused" units to drop down by one unit spacing creating an open position at the top of the stack which may receive a "used" unit. In such embodiments, the compartments of the container may be defined at least in part by the location of units within the container or by spaces which may receive units rather than by structures such as walls. It may be useful to further differentiate "unused" units from "used" units by interposing a movable element such as a shelf or a supporting rod between the two types of units. Such moveable elements may also serve to prevent the removal of a "used" unit through a port intended to dispense "unused" units when the supply of "unused" units within a stack has been exhausted. In addition, a moveable element may provide a visual indication that a stack in which it is present has been depleted.

Figure 3:
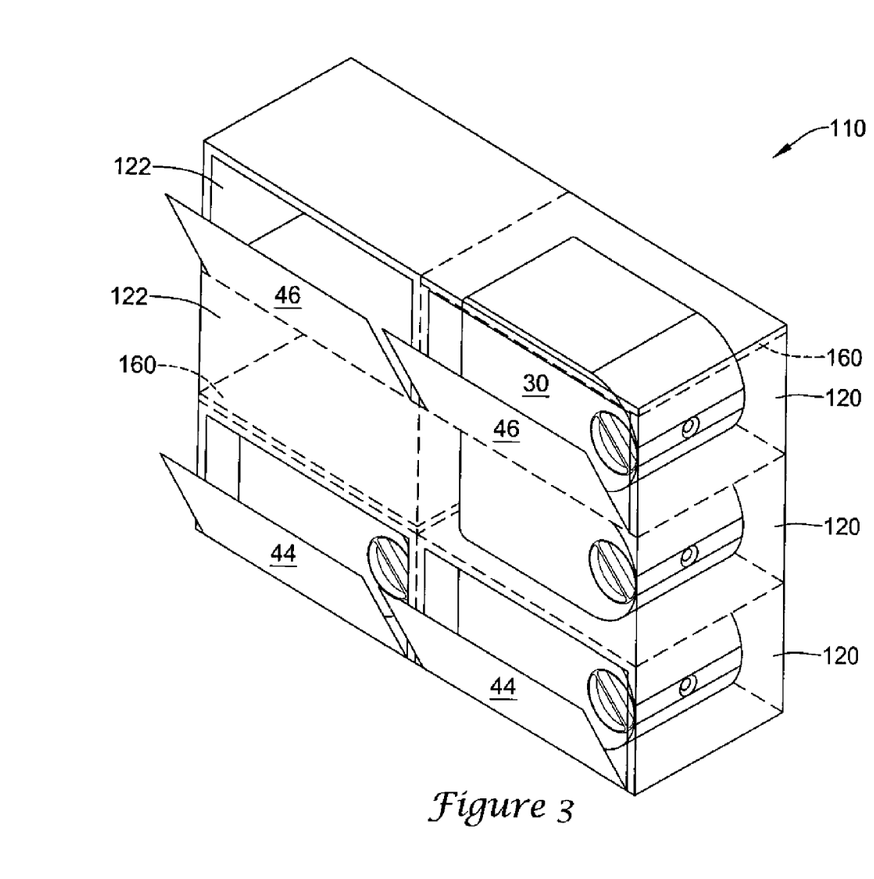
FIG. 3 is a somewhat schematic view of another embodiment of a container for storing, dispensing, and receiving units for storing, dispensing, and receiving medical sharps.

In the embodiment of FIG. 3, container 110 initially houses one or more stacks of units 30 which contain unused pen needle assemblies. As illustrated, the container of FIG. 3 includes two stacks and each of the two stacks includes three compartments. As discussed above, the compartments within the container of any embodiment may be defined by walls, structural elements such as rods or slats, or at least in part by positions within the container which are capable of being occupied by a unit, whether "unused" or "used". Each stack of FIG. 3 is accessible by two doors, a dispensing door 44 for dispensing "unused" units 30 containing unused pen needle assemblies and a receiving door 46 for receiving "used" units 30 which usually contain only used pen needle assemblies. Removing an "unused" unit from the bottom of a stack through door 44 allows any remaining "unused" units and any "used" units which may have been received into the stack through door 46 to move down one compartment. A "used" unit 30 may be introduced into the stack for storage so long as at least one compartment remains unoccupied within the stack. In the case of the left hand stack of FIG. 3 a "used" unit 30 inserted through receiving door 46 would fall immediately into the middle compartment of the stack leaving an empty compartment 122 adjacent to door 46 which could receive a second "used" unit. Removal of the "unused" unit 30 from the compartment adjacent to door 44 would allow the "used" units to move down one position creating an empty compartment adjacent to door 46.

In addition to units, each stack of FIG. 3 includes one or more optional moveable trays 160 which separate the lower "unused" units from the upper "used" units. In addition to separating "unused" units from "used" units, trays may separate individual units from each other if desired. For example, tray 160 in the left hand stack of FIG. 3 may prevent debris and/or liquids associated with a "used" unit introduced above the tray from coming in contact with the "unused" unit(s) which may be stored below the tray. It may be desirable to arrange for the tray to include a sliding seal with the walls surrounding the stack. When a tray 160 reaches the lowest compartment of the stack, it may partially block the port 42 adjacent to door 44 thereby preventing the accidental dispensing of a "used" container and also providing a visual indication that the supply of "unused" units in that stack is exhausted. In some embodiments, a portion of the tray 160 may be visible through one or more apertures in the surrounding container thereby providing an indication of how many unused units remain within the container. It will be appreciated that any given stack may be completely filled with "unused" units; partially filled with "unused" units; completely empty; partially filled with "used" units; completely filled with "used" units; or may contain a mixture of "unused" units, "used" units, and empty compartments at various times during the use cycle of a container.

Although the embodiment depicted is essentially gravity fed, variations of the container may include conveyers which cause units to move within the container. For example, a belt system could be used to move units horizontally or even along a serpentine path within the container rather than downward vertically as illustrated. Such conveyers may be manually operated or may be powered and their motion may be automatically initiated as by a sensor or may be user initiated.

It will also be appreciated that a stack of FIG. 3 may include elements which prevent a unit from moving counter to the normal path of units within the container. These elements may serve to prevent the accidental or intentional removal of a "used" unit from the container. Such elements may include pawls, angled fibers, and the like which tend to limit travel of a container to a single path within the container. Although the descriptions of FIGS. 1 and 3 have assumed that the units are to be inserted directly into compartments within the container, units optionally may be contained within a structure such as a carton or even a sealed sub-container. If such sub-containers are used, they may include elements which interact with travel limiting structures or conveying systems, if present.

Figure 4:
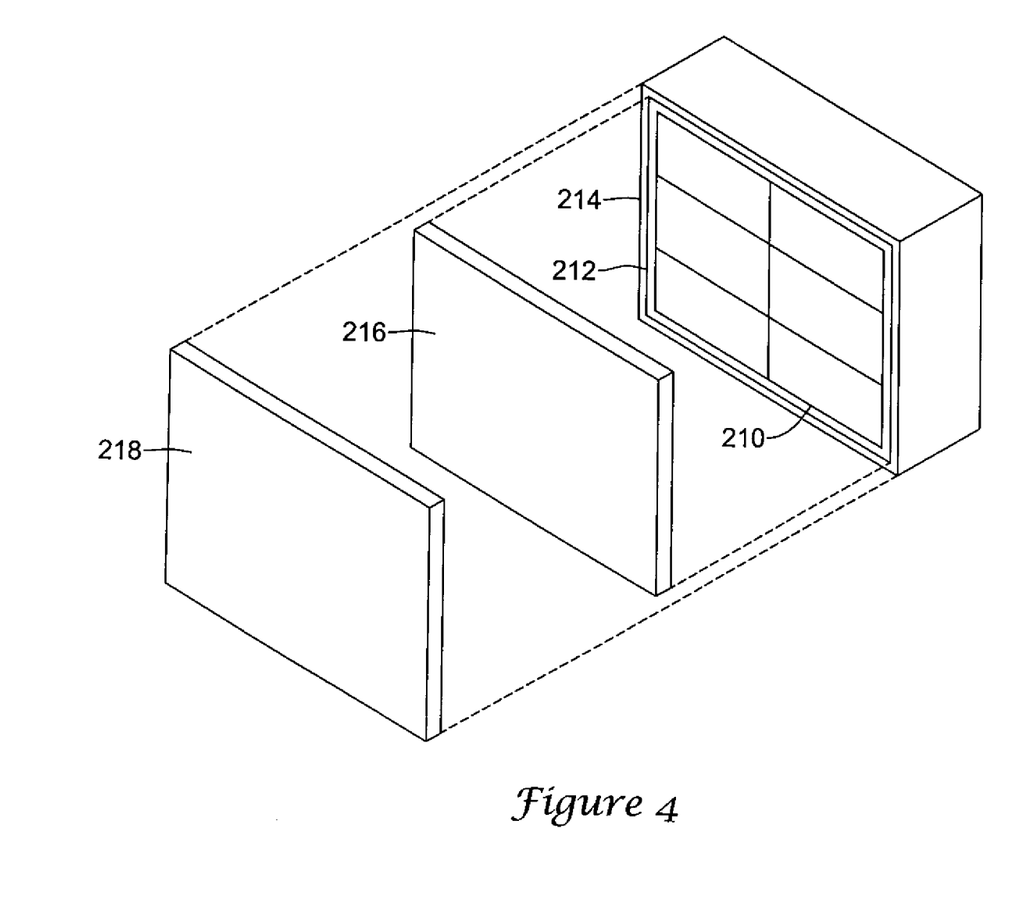
FIG. 4 is a somewhat schematic view of additional containers for use with the containers of the invention.

FIG. 4 illustrates a sealable primary container 212 and a sealable secondary container 214 which may sealably enclose a container 210 for a plurality of units 30 as described above or other embodiments of such containers. The seals employed may be selected to prevent leakage of liquids such as water or even to maintain a seal which is capable of maintaining a pressure differential between the interior and exterior of the container. The primary container and secondary container may be sized and configured to remain in place around the container 210 for storing, dispensing, and receiving units for storing, dispensing, and receiving medical sharps during retail or other dispensing display of the container. The primary and secondary containers may serve as nested one-way or two-way shipping containers for the container 210. Nesting the containers in a display configuration minimizes storage space required at the distribution point which would otherwise have to dedicate shelf space to the container 210 for the units as well as additional space to store the primary and secondary containers 212 and 214 during the time that the container 210 is being used to dispense and receive units. In some embodiments, additional components such as absorbent material, fiberboard containers, and plastic bags or sleeves may be included within or between the primary and secondary containers to comply with applicable mailing or shipping regulations. Together, the container 210, the primary container 212, and the secondary container 214 provide a system which may be used to ship unused medical sharps, such as pen needle assemblies, contained within units for storing, dispensing, and receiving medical sharps to a distribution site such as a retail pharmacy; display and dispense the unused pen needles contained within appropriate units; accept returned units containing used pen needles contained within the now "used" units; seal the used medical sharps within the primary and secondary containers; and forward the used medical sharps to an appropriate facility for the disposal of the contained medical waste.

During the initial distribution of the units containing, for example, unused pen needle assemblies, the primary container 212 and the secondary container 214 may be closed by conventional means or they may be closed by associated covers 216 and 218 respectively. If they are closed by one or both of covers 216 and 218, it is desirable that the covers be conveniently removed at the distribution point and then sealably reinstalled prior to shipping the medical waste disposal facility. This may be accomplished by any of the sealing elements known in the art for this purpose. In some embodiments, the container may include a flange and associated cover and so may eliminate for a primary container while maintaining a doubly sealed shipping configuration. In other embodiments, the individual units may be sealed within their compartments or may be sealed in sub-containers allowing one or both of the primary and secondary containers to be eliminated while still complying with applicable shipping regulations.

Figure 5A:
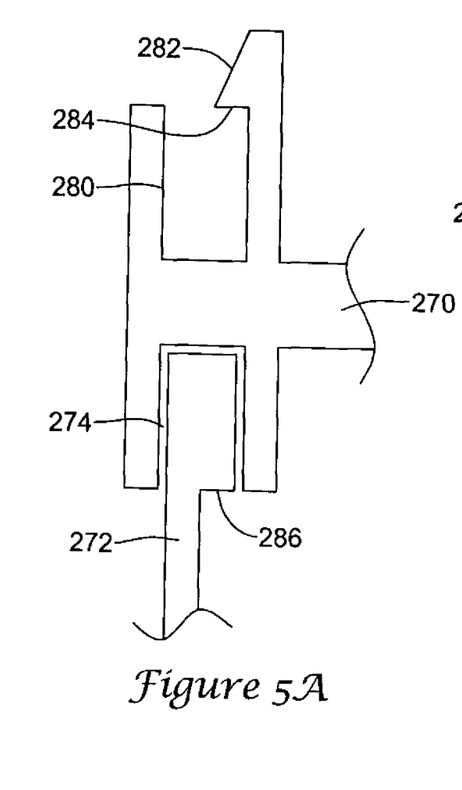
Figure 5B:
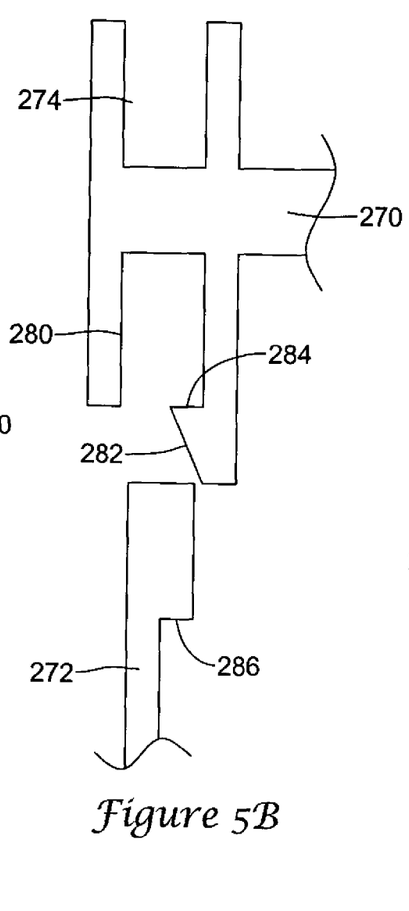
Figure 5C:
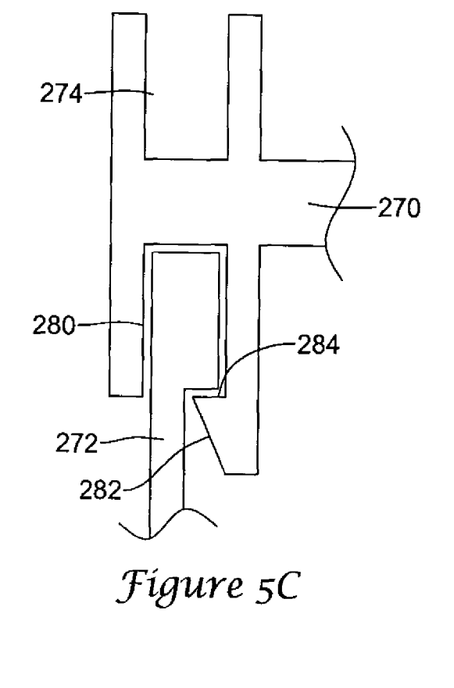

For purposes of illustration, the perimeter seals of FIG. 5A-C, 6A-B, or 7A-B, as well others, may be used to seal the containers or sub-containers described above. The perimeter seal of FIGS. 5A-C may be applied in a first orientation (FIG. 5A) in which a cover 270 is mated to flange 272 to provide a friction fit within perimeter slot 274. If the frictional fit does not provide a sufficient retaining force during shipping, it may be augmented by tape, overwrap, straps, and the like. Upon arrival at the distribution point, the cover may be removed and stored until needed for the second shipping operation. This may conveniently be accomplished by including a storage flange or flanges (not shown) on the face of the outermost container opposite the dispensing opening which may frictionally engage and hold the cover or covers. In alternate configurations, the cover or covers may be hinged or tethered to their container and optionally may be segmented such that the covers 216 and/or 218 may be provided as two or more smaller covers which individually cover only a portion of the openings 212 and/or 214. When the container has been filled with "used" units or otherwise is deemed ready for forwarding to a medical waste disposal facility, the cover(s) may be removed from storage and positioned over the front flange(s) as illustrated in FIG. 5B. Flange 272 is then pressed against inclined surface 282 until the flange enters slot 280 and mating surfaces 284 and 286 engage to lock the cover in place on the flange. If desired, one or both of slots 274 and 280 may be provided with seals such as O-rings (not shown).

Figure 6A:
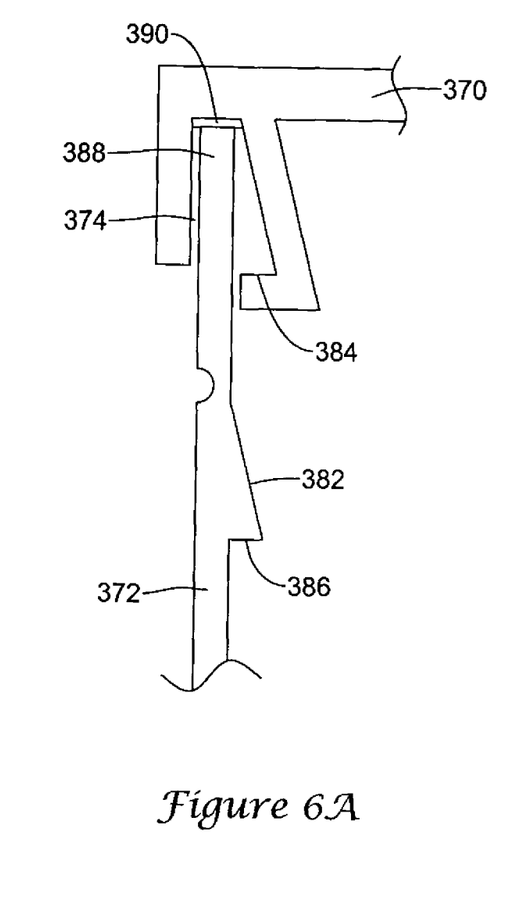
Figure 6B:
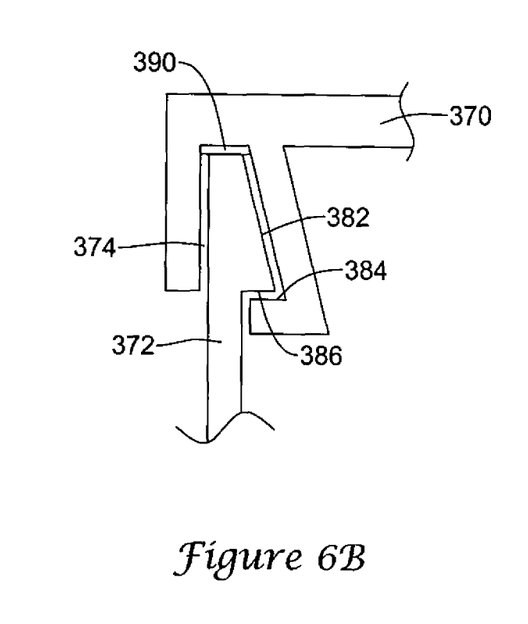

FIGS. 6A and 6B illustrate a variant dual purpose flange and cover system. In FIG. 6A, the cover 370 is disposed with slot 374 frictionally engaged with removable strip 388 of flange 372 in an initial shipping configuration. It may be readily removed at the distribution point and reinstalled if that becomes desirable. When the container has been filled with "used" units or otherwise is deemed ready for forwarding to a medical waste disposal facility, strip 388 may be torn from flange 372. The cover(s) 370 may be removed from storage and positioned over the flange(s) 372 and urged toward the container over inclined surface 382 until mating surfaces 384 and 386 engage as illustrated in FIG. 6B. If desired, a seal 390 may be included.

Figure 7A:
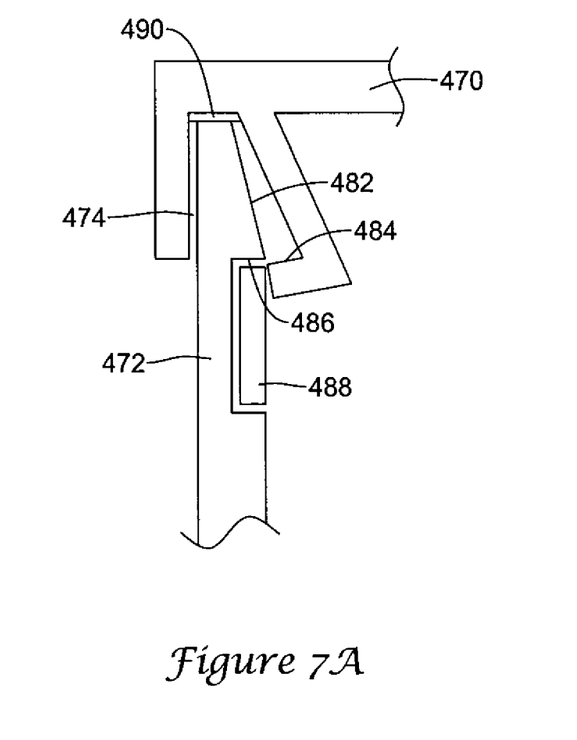
Figure 7B:
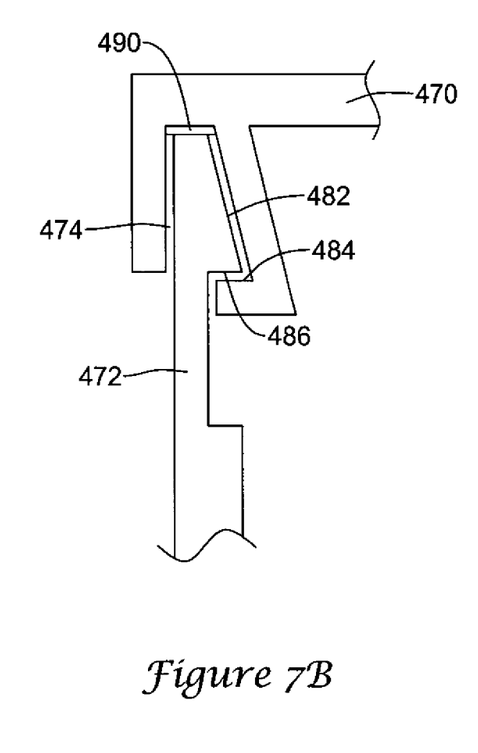

FIGS. 7A and 7B illustrate another variant dual purpose flange configuration which may be used to seal any of the containers or sub-containers described above. In FIG. 7A, the cover 470 is disposed with slot 474 frictionally engaged with flange 472 and removable strip 488. The cover may be readily removed and reinstalled as long as strip 488 remains in place. When the container has been filled with "used" units or otherwise is deemed ready for forwarding to a medical waste disposal facility, strip 488 may be torn from flange 472. The cover(s) 470 may be removed from storage and positioned over the flange(s) 472 and urged toward the container over inclined surface 482 until mating surfaces 484 and 486 engage as illustrated in FIG. 7B. If desired, a seal 490 may be included.

As noted earlier, the container and its operation may readily be adapted to accommodate a variety of units for storing, dispensing, and receiving medical sharps. The size and configuration of units which are known at present or which may become available may be readily accommodated by changes in the dimensions of the compartments within the container. Although the embodiments selected for illustration purposes have each comprised two columns of three rows of compartments and have been accessed from a single face of the container, it will be appreciated that the container may have any number of rows, columns, and depth layers and may be accessible through more than one face. For example, the container may include four rows and four columns of compartments in each of two layers which open on two or more faces of a rectangular prism.

The operation of the container is not influenced by the nature of the medical sharps which are to be dispensed and returned to the unit after use. Accordingly, the units may contain pen needle assemblies, hypodermic needles, syringes including hypodermic needles, lancets, and the like as well as mixtures thereof. Although the description of units provided above has focused upon dual purpose devices which provide both the dispensing and the receiving functions in a single housing, it will be appreciated that unit, as used herein, may also include separable components for the dispensing and receiving functions if desired. For example, the supply of unused medical sharps may be contained within a housing during the distribution phase and may be removed as a separate element of the unit by the end user who then uses the housing as the receiving element which will be returned to the container for consolidation and disposal.

The system of the disclosure may be used in the following manner. An empty container may be filled with a plurality of "unused" units for storing, dispensing, and receiving medical sharps by placing a single unit in each compartment within the container. Optionally, the container may be placed within primary or even secondary containers and any desired shipping materials. If primary or secondary containers are used, they may be fitted with removable covers to protect the contents from contamination or damage during distribution. Upon arrival at a retail outlet or other distribution point, the covers may be removed to provide access to the container for a plurality of units for storing, dispensing, and receiving medical sharps. At this time the additional shipping materials may be removed for separate storage or may be left in place surrounding the container. The container may then be used to dispense individual units to the end user. When the end user has used the medical sharps and returned the used medical sharps to the unit, it may be returned to a retail outlet or other distribution point where it will be inserted into a compartment of a container. Some distribution points may wish to impose a deposit on each unit to encourage proper disposal of the "used" units.

It will be appreciated that the container to which a "used" unit is returned is not necessarily the same container from which it was initially dispensed due to the normal turnover of units dispensed by the retail outlet or other distribution point and the delay introduced by the time required to use the plurality of medical sharps contained within the unit. In some instances, a unit may be returned to a different retail outlet or other distribution point than the one from which it was originally obtained. This may be accommodated by the sale or distribution of a replacement unit which will create a vacant compartment within the container. In some embodiments, it may be desirable to include one or more empty compartments in at least some containers to accommodate disparities between the numbers of units dispensed by an outlet and units received by the outlet.

When sufficient "used" units have been returned to a container, usually filling each of the compartments, the container may be sealed within one or more outer containers and shipped to a facility for the destruction of medical waste. Depending upon the design of the components of the overall sharps disposal system, the container may become sealed and may require only one additional container and sealing cover element or the container may remain unsealed and may be sealed within primary and secondary containers. In either construction, the sealed outer container may be provided with the required labels and additional shipping materials as required by mailing and/or shipping regulation.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. A storing, dispensing, and receiving container for units for storing, dispensing, and receiving medical sharps comprising:
    an outer container further comprising:
        a plurality of compartments, said compartments each being capable of containing one unit for storing, dispensing, and receiving medical sharps,
        wherein the container is adapted to store and dispense units containing unused sharps; and
        wherein the container is adapted to receive and store units containing used medical sharps,
        further wherein the container is adapted to differentiate units containing unused sharps from units containing used sharps.

2. The container of claim 1, wherein the medical sharps are pen needles.

3. The container of claim 1, wherein the medical sharps are hypodermic needles.

4. The container of claim 1, wherein the units are each adapted to dispense unused medical sharps and to receive used medical sharps.

5. The container of claim 1, wherein the units dispensed by the container are generally similar to the units received by the container except for the condition and location of the medical sharps within the individual units.

6. The container of claim 1, further comprising a dispensing port capable of providing access to a compartment containing a unit which contains unused medical sharps such that said unit may be removed from the compartment.

7. The container of claim 6, wherein the dispensing port capable of providing access to a compartment containing a unit which contains unused medical sharps is not capable of allowing a unit containing used medical sharps to be inserted into the compartment to which the port provides access.

8. The container of claim 1, further comprising a receiving port capable of providing access to a compartment which does not contain a unit for storing, dispensing, and receiving medical sharps such that a unit containing used medical sharps may be inserted into the compartment.

9. The container of claim 1, further comprising a moveable partition separating units containing unused sharps from units containing used sharps.

10. The container of claim 1, wherein the compartments are defined at least in part by the positions of units within the container.

11. The container of claim 1, wherein removing a unit containing unused medical sharps from a container compartment creates a compartment within the container which may receive a unit containing used medical sharps.

12. The container of claim 11, wherein the compartment which may receive a unit containing used medical sharps and the compartment created by the removal of a unit containing unused medical sharps do not occupy the same position within the container.

13. The container of claim 11, wherein the removal of a unit containing unused medical sharps causes at least one unit within the container to move toward the position from which the unit containing unused medical sharps was removed by a distance corresponding to a dimension of one compartment.

14. The container of claim 1, further comprising at least one sealing element which are positionable to make the container water tight.

15. The container of claim 14, wherein the at least one sealing element is positionable to allow the container to maintain a positive internal pressure.

16. The container of claim 1, further containing a liquid absorbing element.

17. The container of claim 1, further comprising an outer sealable container capable of containing the container.

18. A system for distributing and dispensing unused sharps and returning used sharps comprising:
    a plurality of units for storing, dispensing, and receiving medical sharps;
    a container for the plurality of units for storing, dispensing, and receiving medical sharps, said container including a plurality of compartments, each compartment being capable of containing one unit for storing, dispensing, and receiving medical sharps, further wherein the container is adapted to differentiate units containing unused sharps from units containing used sharps;

a primary container capable of receiving and sealably containing the plurality of units; and a secondary container capable of receiving and sealably containing the primary container.

19. The system of claim 18, wherein the container is the primary container.

20. The system of claim 18, wherein the secondary container is further contained within a shipping container.

21. A method of distributing unused medical sharps and collecting used medical sharps comprising:

providing a plurality of units for storing, dispensing, and receiving medical sharps;

providing a container for the plurality of units for storing, dispensing, and receiving medical sharps, said container including a plurality of compartments, each compartment being capable of containing one unit for storing, dispensing, and receiving medical sharps;

inserting a unit for storing, dispensing, and receiving medical sharps into at least one compartment of the container;

distributing the container containing the plurality of units;

dispensing a unit containing unused medical sharps from the container;

receiving a unit containing used medical sharps;

inserting a unit containing used medical sharps into the container;

sealing the container;

sealing the container within a secondary container; and shipping the sealed container and secondary container containing a plurality of units containing used medical sharps to a facility for destruction of the used medical sharps.

22. The method of claim 21, wherein the container includes a plurality of compartments, said compartments each being capable of containing one unit for storing, dispensing, and receiving medical sharps.

23. The method of claim 21, wherein removing a unit containing unused medical sharps from the container allows at least one unit within the container to move to a different compartment within the container.

24. The method of claim 23, wherein the movement of at least one unit within the container is accompanied by the movement of a partition separating one or more compartments containing units containing unused medical sharps from one or more compartments containing units containing used medical sharps.

25. The method of claim 21, wherein the compartments are defined at least in part by the positions of units within the container.

26. The method of claim 21, wherein dispensing a unit containing unused medical sharps from the container further comprises opening a port in the container and removing a unit.

27. The method of claim 26, wherein the port is sealable.

28. The method of claim 21, wherein inserting a unit containing used medical sharps further comprises opening a port and inserting the unit into an empty compartment.

29. The method of claim 28, wherein the port is sealable.

30. The method of claim 21, wherein each compartment is sealable following the insertion of a unit containing used medical sharps.

* * * * *